(12) United States Patent
Adams

(10) Patent No.: US 6,312,438 B1
(45) Date of Patent: Nov. 6, 2001

(54) ROTARY BUR INSTRUMENTS HAVING BUR TIPS WITH ASPIRATION PASSAGES

(75) Inventor: Kenneth M. Adams, Jacksonville, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

(21) Appl. No.: 09/495,350

(22) Filed: Feb. 1, 2000

(51) Int. Cl.[7] .................................................... A61B 17/22
(52) U.S. Cl. ............................................................. 606/159
(58) Field of Search .................................. 606/159, 180, 606/170, 171, 169; 604/22

(56) References Cited

U.S. PATENT DOCUMENTS

| 4,203,444 | 5/1980 | Bonnell et al. . |
| 4,445,509 | 5/1984 | Auth . |
| 4,466,429 | 8/1984 | Loscher et al. . |
| 4,517,977 | 5/1985 | Frost . |
| 4,646,738 | 3/1987 | Trott . |
| 5,007,917 | 4/1991 | Evans . |
| 5,123,904 | 6/1992 | Shimomura et al. . |
| 5,152,744 | 10/1992 | Krause et al. . |
| 5,322,505 | 6/1994 | Krause et al. . |
| 5,366,468 | 11/1994 | Fucci et al. . |
| 5,383,884 | 1/1995 | Summers . |
| 5,556,405 | * 9/1996 | Lary ........................................ 606/159 |
| 5,759,185 | * 6/1998 | Grinberg .............................. 606/180 |
| 5,913,867 | 6/1999 | Dion . |
| 5,922,003 | 7/1999 | Anctil et al. . |
| 6,015,420 | * 1/2000 | Wulfman et al. ..................... 606/159 |

OTHER PUBLICATIONS

Aesculap®—Arthroscopy System, Product catalog, 16 pages, AESCULAP–WERKE AG, 7200 Tuttlingen/FRG, 2/88.
Smith & Nephew Endoscopy 1996 Product Catalog, 3 pages, Jan. 1, 1996.

* cited by examiner

Primary Examiner—Kevin Truong

(57) ABSTRACT

A rotary bur instrument includes an outer tube having an open distal end, and an inner member rotatably disposed in the outer tube. The inner member includes an inner tube having a distal end, a lumen therethrough and a bur tip at the distal end of the inner tube. The bur tip extends distally from the open distal end of the outer tube and has a passage extending longitudinally therethrough in communication with the lumen of the inner tube. The passage and the lumen define an aspiration passage through the inner member communicating with an aspiration port at a distal end of the bur tip.

48 Claims, 2 Drawing Sheets

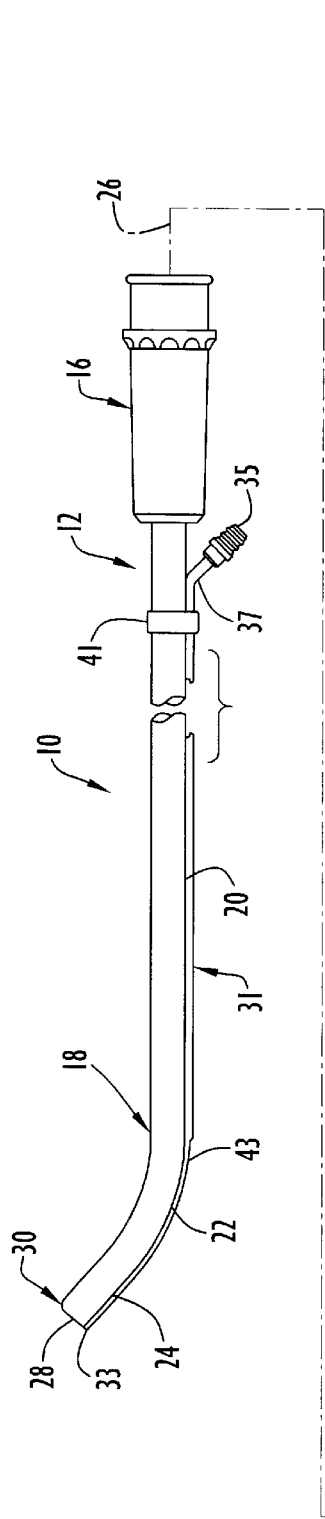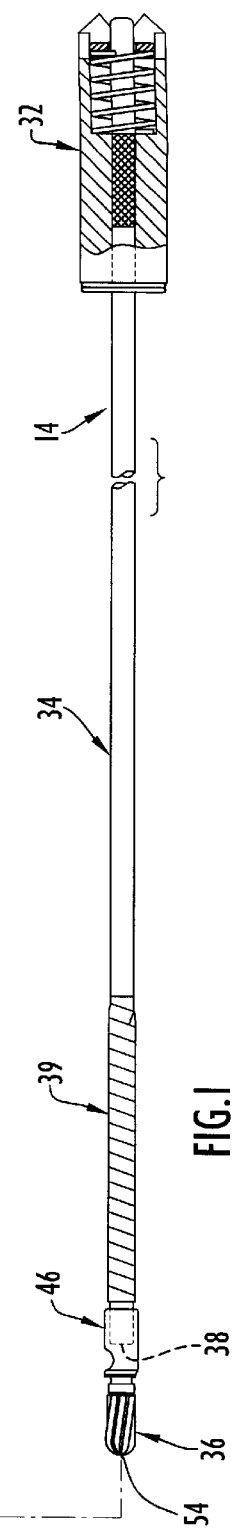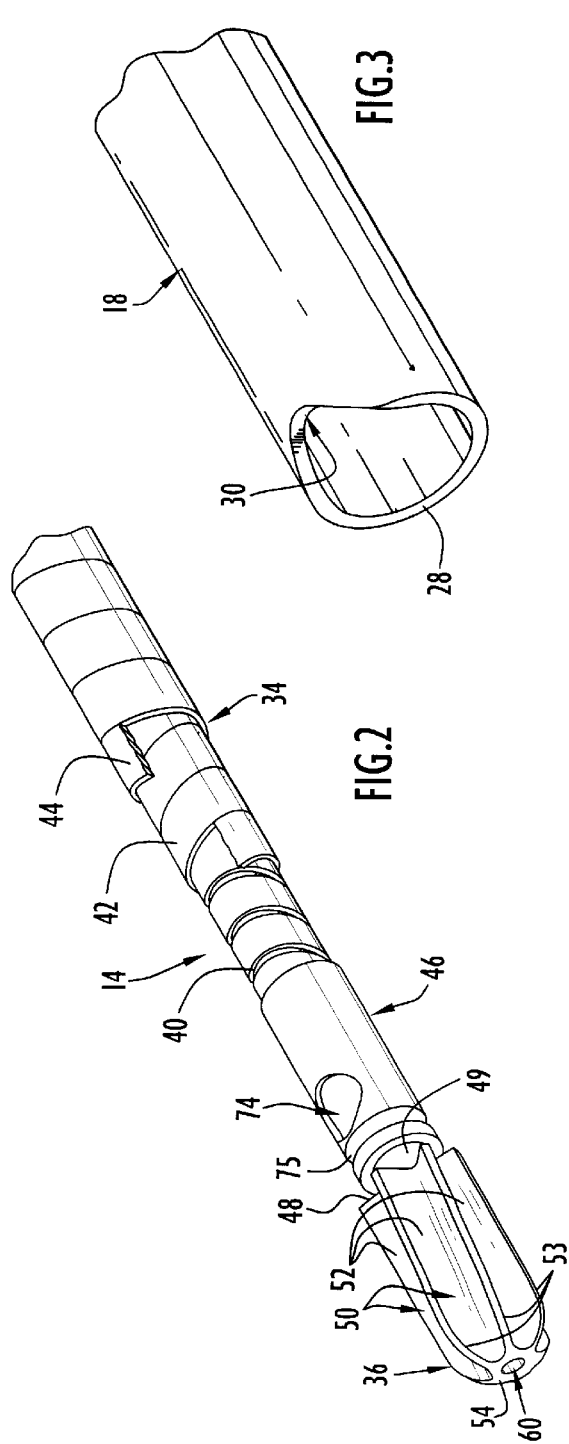
FIG.1
FIG.2
FIG.3

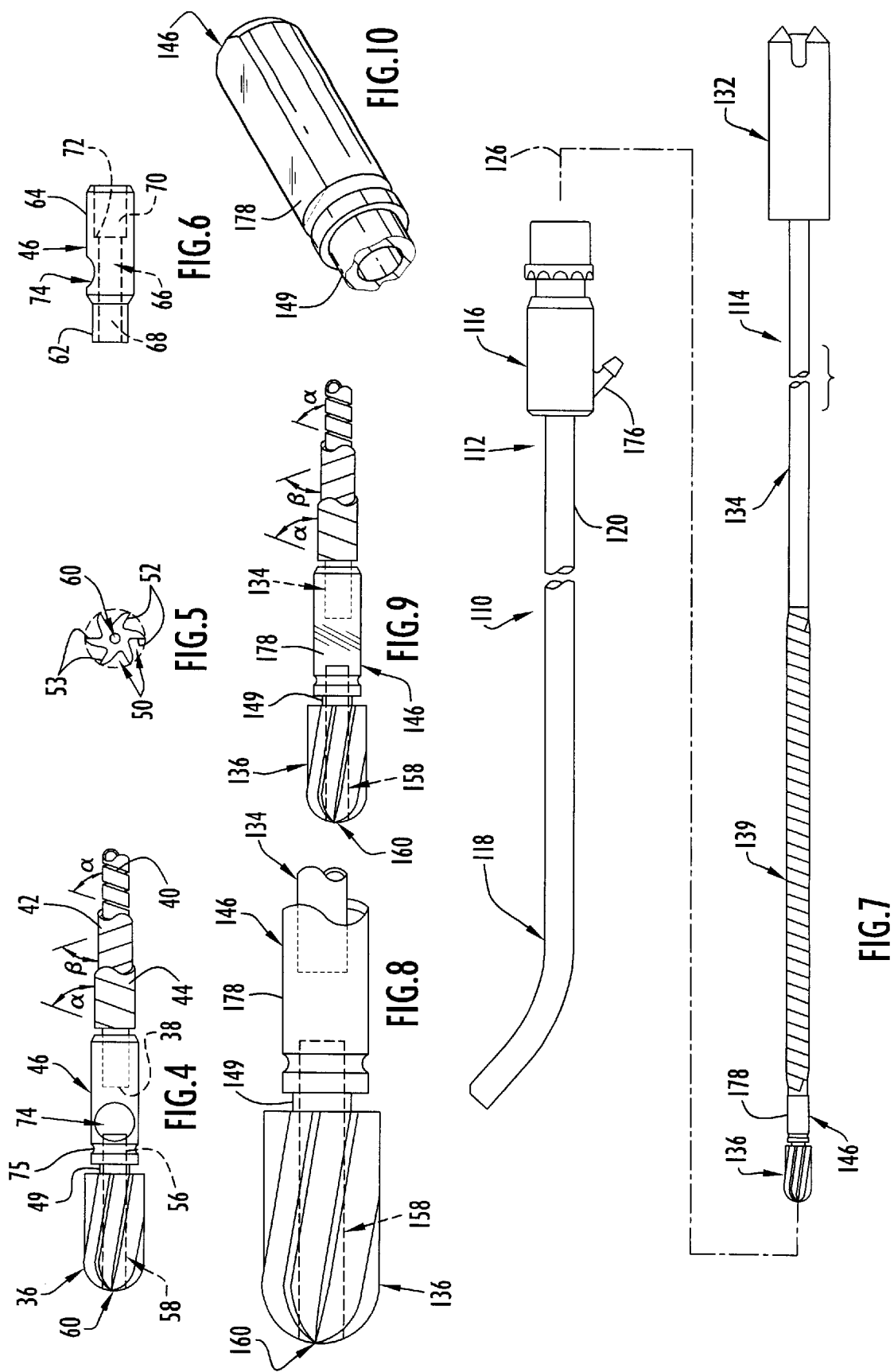

ROTARY BUR INSTRUMENTS HAVING BUR TIPS WITH ASPIRATION PASSAGES

CROSS-REFERENCE TO RELATED APPLICATIONS

This application is related to prior applications Ser. No. 09/005,010, filed Jan. 9, 1998, and now U.S. Pat. No. 5,957,945, and Ser. No. 09/404,461 filed Sep. 24, 1999, the disclosures of which are incorporated herein by reference.

BACKGROUND OF THE INVENTION

1. Field of the Invention

The present invention relates generally to rotary bur instruments used for tissue removal and, more specifically, to rotary bur instruments having suction or aspiration passages for removing debris resulting from cutting procedures.

2. Discussion of the Related Art

Surgical cutting instruments in which an elongate inner member is rotated within an elongate, tubular outer member have become well accepted in surgical procedures where access to a surgical site is gained via a narrow portal or passage. Typically, the tubular outer member includes a distal end with an opening, and the inner member includes a distal end with a cutting tip for engaging bodily tissue via the opening. Proximal ends of the inner and outer members commonly include hubs which attach to a handpiece having a motor for rotating the inner member relative to the outer member. The distal end of the inner member can have various configurations dependent upon the cutting procedure to be performed. Often the inner member is tubular so that debris resulting from the cutting procedure can be aspirated through the inner member. It is also common for the direction of rotation of the inner member to be reversible during operation. An example of a rotary tissue cutting instrument of the aforementioned type is described in U.S. Pat. No. 4,203,444 to Bonnell et al for use in performing arthroscopic knee surgery. Other rotary tissue cutting instruments having longitudinal aspiration through the instruments are disclosed in U.S. Pat. Nos. 5,383,884 to Summers, 5,366,468 to Fucci et al, 5,123,904 to Shimomura et al, 5,007,917 to Evans and 4,517,977 to Frost.

The tubular inner and outer members disclosed in the Bonnell et al patent are straight. In many surgical procedures, however, it is desirable for the cutting instruments to be bent, angled or curved to access surgical sites which are generally not accessible with straight cutting instruments. Rotary tissue cutting instruments with curved or bendable shafts are exemplified by U.S. Pat. Nos. 5,922,003 to Anctil et al, 5,322,505 and 5,152,744 to Krause et al, 4,646,738 to Trott, 4,466,429 to Loscher et al and 4,445,509 to Auth.

In the area of head and neck surgery and, in particular, sinus surgery, rotary tissue cutting instruments having burs for the cutting tips have been used for tissue removal, such as removal of bone from a patient's nasal frontal beak. Some rotary bur instruments are angled in that the outer members or shafts thereof have an angle, bend or curve. Prior rotary bur instruments have encountered numerous problems, a primary problem being clogging or jamming of the instruments from debris or tissue buildup. Jamming or clogging of the instruments leads to the need for frequent cleaning or substitution of the instruments during use, which is time consuming thus increasing the duration of the procedure and which contributes to physician fatigue thus increasing the chance of error.

Some rotary bur instruments employed in sinus surgery have aspiration ports proximally of the bur tips for evacuating debris, such as bone, blood and irrigation fluid, via the instruments to deter jamming and clogging. U.S. Pat. No. 5,913,867 to Dion is illustrative of a rotary bur instrument having longitudinally straight inner and outer members or shafts and having an aspiration port proximally of a bur tip. The position of the aspiration ports proximally of the bur tips in prior rotary bur instruments results in aspiration of debris in the immediate vicinity of the aspiration ports while allowing debris to accumulate around and in front of the bur tips. The bur tips are thus difficult to view with endoscopes as typically utilized in sinus procedures.

U.S. Pat. No. 5,759,185 to Grinberg shows a rotary bur instrument having longitudinally straight inner and outer members or shafts and having a bur tip with an interior chamber communicating with a suction passage in the instrument. The interior chamber also communicates with apertures in flutes of the bur tip but does not extend to a distal end of the bur tip. Therefore, suction is not present in front of or at the distal end of the bur tip, giving rise to the problems of debris accumulation and decreased visibility discussed above.

A particular problem of angled rotary bur instruments relates to the external diametric or cross-sectional sizes needed for the angled, curved or bent outer members or shafts to accommodate the structure or components used to enable the inner members or shafts to rotate within the outer members or shafts. The external diametric or cross-sectional sizes of the outer members of prior angled rotary bur instruments are typically larger than desirable, thereby decreasing visibility of the operative site or area by the surgeon and reducing the amount of free area or room available to the surgeon in which to maneuver the angled rotary bur instruments and the endoscopes.

A further problem of prior angled rotary bur instruments is that access to various operative sites or areas is limited by the size of the angles and/or by the locations of the angles, curves or bends in the outer members. The sizes and/or locations for the angles, curves, or bends in prior angled rotary bur instruments is generally dictated by the structure or components used to enable rotation of the inner members within the non-straight outer members. Accordingly, many prior angled rotary bur instruments are unable to meet the needs of surgeons for various angles or ranges of angles for the outer members as well as various locations on the outer members for the angles, bends or curves.

SUMMARY OF THE INVENTION

Accordingly, it is a primary object of the present invention to overcome the above mentioned disadvantages of prior art rotary bur instruments, whether straight or angled, and to improve rotary bur instruments used for tissue removal and, in particular, those used in surgery of the head and neck and other parts of the body.

It is another object of the present invention to provide suction at a distal end of a bur tip of a rotary bur instrument via an aspiration or suction port formed in the distal end of the bur tip.

It is yet another object of the present invention to deter the accumulation of debris at the distal end of a bur tip of a rotary bur instrument.

Still another object of the present invention is to enhance endoscopic visualization of a bur tip of a rotary bur instrument in sinus procedures.

The present invention also has as an object to remove bone from a patient's nasal frontal beak trans-septally or ipsi-laterally.

An additional object of the present invention is to increase the available area in which to maneuver a rotary bur instrument and an endoscope in sinus procedures.

Yet a further object of the present invention is to reduce the external diametric or cross-sectional size of an outer member of an angled rotary bur instrument.

The present invention has as an additional object to provide a longitudinal suction or aspiration passage entirely through a bur tip of a rotary bur instrument.

It is also an object of the present invention to provide a rotary bur instrument having an aspiration passage communicating with an aspiration port at a distal end of a bur tip and communicating with an aspiration port disposed proximally of the bur tip.

Some of the advantages of the present invention are that jamming and clogging of the rotary bur instruments are avoided, unexpected clogging can be easily and quickly cleared by pushing a stylette or other suitable member through the bur tip to reach the clog or obstruction, various cannulated bur tips can be coupled to the inner members via adapters, the inner members and/or bur tips are maintained concentric with the outer members while being rotated relative to the outer members, the outer members can be provided or formed with various angles, bends or curves, irrigating fluid can be supplied to an operative site or area via the rotary bur instruments, irrigating fluid can be supplied through the rotary bur instruments to the operative site or area, and the rotary bur instruments can be driven or powered by various surgical handpieces capable of rotating an inner member relative to an outer member.

These and other objects, advantages and benefits are realized with the present invention as generally characterized in a rotary bur instrument comprising an outer member having an open distal end and an inner member rotatably disposed within the outer member. The inner member includes an inner tube having a distal end, a lumen extending therethrough and a bur tip disposed at the distal end of the inner tube. The bur tip extends distally from the open distal end of the outer tube and has a distal end, a passage extending therethrough and a distal aspiration port at the distal end of the bur tip communicating with the passage. The passage and the lumen are in communication and define an aspiration or suction passage through the inner member by which debris, such as tissue, blood and saline, is aspirated via the distal aspiration port. In one embodiment, the inner member also has a proximal aspiration port communicating with the aspiration passage and disposed proximally of a bur body of the bur tip. The proximal aspiration port may be formed in an adapter coupling the bur tip to the inner tube. The instrument may further include an irrigation passage, which may extend externally or internally along the instrument. The proximal aspiration port may be exposed by the outer tube a variable amount depending on the rotational position of the inner member relative to the outer member. As an example, the proximal aspiration port may be exposed a maximum amount when the inner member is in a first rotational position and less than the maximum amount when the inner member is in a second rotational position. The second rotational position can coincide with a discharge end of the irrigation passage to avoid suction at the proximal aspiration port from interfering with the discharge of irrigating fluid from the irrigation passage. The outer member may be angled, bent or curved, and the inner member may be provided with a flexible region adjacent the angle, bend or curve by which the inner member is capable of rotating within the outer member.

Other objects and advantages of the present invention will become apparent from the following description of the preferred embodiments taken in conjunction with the accompanying drawings, wherein like parts in each of the several figures are identified by the same reference numerals or by reference numerals having the same last two digits.

BRIEF DESCRIPTION OF THE DRAWINGS

FIG. 1 is a broken exploded side view of a rotary bur instrument according to the present invention.

FIG. 2 is an enlarged fragmentary perspective view, partly cut away, of a distal portion of an inner member of the rotary bur instrument.

FIG. 3 is an enlarged fragmentary perspective view of a distal portion of an outer member of the rotary bur instrument.

FIG. 4 is a fragmentary top view of the distal portion of the inner member.

FIG. 5 is an end view of a bur tip for the rotary bur instrument.

FIG. 6 is a side view of an adapter for the rotary bur instrument.

FIG. 7 is a broken exploded side view of an alternative rotary bur instrument according to the present invention.

FIG. 8 is a fragmentary side view of the distal portion of an inner member of the alternative rotary bur instrument according to the present invention.

FIG. 9 is a fragmentary top view of the distal portion of the inner member of the alternative rotary bur instrument.

FIG. 10 is a fragmentary perspective view of an adapter and bur tip of the alternative rotary bur instrument.

DETAILED DESCRIPTION OF THE PREFERRED EMBODIMENTS

A rotary bur instrument 10 according to the present invention, as illustrated in FIG. 1, includes an elongate outer member 12 and an elongate inner member 14 rotatably received within the outer member. The rotary bur instrument 10 is illustrated as an angled rotary bur instrument having an angled, bent or curved outer tube and an inner tube including a flexible region adjacent the angle, bend or curve. However, it should be appreciated that the rotary bur instrument 10 can include longitudinally or axially straight inner and outer tubes without angles, bends or curves and that the inner tube need not be flexible. That is, where the outer tube is straight, the inner tube can be rigid. Outer member 12 includes an outer hub 16 and a rigid outer tube or shaft 18 having a proximal length portion 20 of longitudinally or axially straight configuration extending distally from the hub to a bend, angle or curve 22 connecting the proximal length portion with a distal length portion 24 oriented at an angle relative to a central longitudinal axis 26 of the proximal length portion. Distal length portion 24 of the outer tube extends upwardly from bend 22, looking at FIG. 1, to an open distal end 28 defining an opening circumscribed by a peripheral or circumferential edge. A curved recess, notch or indentation 30, best shown in FIG. 3, is formed in outer tube 18 along the circumferential edge, the recess 30 extending in a proximal direction and being disposed at the top of the outer tube when the outer member is oriented as shown in FIG. 1. The radius of curvature, the size of the bend angle and the location of the bend relative to the distal end 28 are dependent upon the procedure to be performed and the location of an operative site or area to be accessed. Preferably, the bend angle for bend 22 is in the range of 0 to 70 degrees and, more preferably, the bend angle is 40 degrees.

The instrument 10 includes an irrigation passage defined by an irrigation or injector tube 31 extending externally alongside the outer tube 18. The irrigation tube has an open distal end 33 defining a discharge end for the irrigation passage and disposed adjacent or in alignment with the distal end of the outer tube, an open proximal end connected to a fitting 35, and an irrigation channel or lumen between the distal and proximal ends of the irrigation tube. The open distal end 33 of the irrigation tube is disposed along the peripheral or circumferential edge of the outer tube at a location diametrically opposite, i.e. 180° from, the center of recess 30 so that the distal end 33 is located at the bottom of the outer tube when the outer member is oriented as shown in FIG. 1. The irrigation tube 31 follows or substantially follows the longitudinal configuration of the outer tube and is disposed close to the outer tube except for a proximal angled or bent portion 37 of the irrigation tube. The angled portion extends outwardly from the outer tube and terminates at the open proximal end of the irrigation tube, which is disposed within the fitting. The irrigation tube is attached to the outer tube at one or more locations.

In the case of outer member 12, a distal length portion 43 of irrigation tube 31 is flattened, the flattened distal length portion extending from the irrigation tube distal end to terminate a short distance proximally of the bend 22 and being secured to the outer tube by welding. The flattened distal length portion reduces the overall cross-sectional size of the distal potion of the instrument providing increased space at an operative site for visualization and manipulation. The irrigation tube is of sufficient length so that the fitting is disposed externally of a patient's body when the distal end of the rotary bur instrument is disposed at an operative site or area in the patient's body. As shown in FIG. 1, the proximal end of the irrigation tube is disposed distally of but near the hub 16. The fitting can be of various types suitable, for example, for connection with a length of flexible tubing coupled with a source or supply of irrigation fluid such as saline. Accordingly, irrigation fluid from the source is supplied through the tubing, the fitting and the irrigation tube for discharge at the distal end of the outer tube.

In a preferred embodiment, the outer tube is made of Type 304L stainless steel tubing, ¾ hard, with an inner diameter of about 0.125 inch and an outer diameter of about 0.146 inch. The proximal end of the outer tube is attached to hub 16 in a conventional manner using a raised fine diamond knurl at the proximal end of the outer tube as a point of attachment. The outer tube has an overall length, prior to attachment to the hub 16, of about 4.540 inches. The irrigation tube is made of Type 304L stainless steel, ½ hard, having an inner diameter of about 0.042 inch and an outer diameter of about 0.058 inch. The irrigation tube has a length of about 3.780 inches from the distal end thereof to the start of the proximal angled portion 37, which is disposed at an angle of about 45 degrees relative to the longitudinal axis 26. The irrigation tube is attached to the outer tube by having the flattened distal length portion laser welded to the outer tube. Also, a collar 41 of shrink tubing is disposed around the irrigation tube and the proximal length portion of the outer tube to maintain the irrigation tube in close proximity to the outer tube. As shown in FIG. 1, the collar 41 is located near the proximal angled portion of the irrigation tube. The fitting of the preferred embodiment is made of Natural ABS and is bonded, using Loctite, to the proximal end of the irrigation tube.

Inner member 14 includes an inner hub 32 disposed proximally of the outer hub 16 when the inner member 14 is disposed within the outer member 12, an elongate inner tube or shaft 34 extending distally from the hub 32 to be disposed coaxially or concentrically within the outer tube and a bur tip 36 at a distal end of inner tube 34. Inner tube 34 is of hollow, cylindrical configuration and terminates distally at a distal end 38, which is coupled with bur tip 36. A lumen is defined within and along the length of inner tube 34. Also, the inner tube 34 has a flexible region 39 adjacent or disposed within the bend 22 in the outer member to permit the inner member to bend while rotating within the outer member. In the case of inner member 14, the flexible region 39 is provided or formed in the manner described below and disclosed in prior application Ser. No. 09/404,461 filed Sep. 24, 1999, the disclosure of which is incorporated herein by reference. However, the flexible region can be provided or formed in various other ways, including that disclosed in U.S. Pat. No. 5,922,003 to Anctil et al, the disclosure of which is incorporated herein by reference.

As shown in FIGS. 2 and 4, a spiral or helical cut 40 is formed through the inner tube 34 along a length portion thereof corresponding to the flexible region. Spiral cut 40 is shown with a left hand turn; that is, the cut extends counterclockwise around the inner tube 34 and is oriented at an angle a relative to the central longitudinal axis of the inner tube. The cut extends continuously without interruption between the start and end thereof and terminates distally at a distal location a short distance proximally of distal end 38 and proximally at a proximal location proximally of bend 22. The uncut portion of inner tube 34 distally of the cut 40 is of sufficient length to permit the inner tube to be coupled with the bur tip via an adapter as explained below while allowing the inner tube to bend or flex just proximally of the adapter thereby facilitating use of the rotary bur cutting instrument in hard to reach areas sometimes encountered in surgery of the head and neck and other parts of the body.

Inner tube 34 further includes a pair of spirally wound strips 42 and 44 superimposed over the spirally cut region. Strips 42 and 44 are formed of a resilient or elastic material, such as stainless steel, and preferably have a rectangular cross-section allowing the strips to lay flat when wrapped around the spirally cut region of the inner tube. As shown in FIGS. 2 and 4, the innermost strip 42 is wrapped in a direction opposite that of spiral cut 40; and, therefore, the innermost strip 42 is wrapped with a right hand turn. Accordingly, the innermost strip extends around the inner tube in a clockwise direction. The outermost strip 44 is wrapped around the inner tube in a direction opposite that of the innermost strip so that it is wrapped with a left hand turn and extends around the inner tube in a counterclockwise direction, the outermost strip being wrapped around the innermost strip. The innermost and outermost strips are angled relative to one another (e.g., at supplementary angles relative to the longitudinal axis of the inner tube) so as to overlap one another, thereby allowing partial vacuum to be maintained in the lumen defined by the inner tube. As shown in FIG. 4, the innermost strip 42 is oriented at an angle $\beta$ which is the supplement of angle $\alpha$ (i.e., 180° minus $\alpha$) of the spiral cut, and the outermost strip 44 is oriented at the same angle $\alpha$ as the spiral cut. Opposite ends of the strips 42 and 44 are secured to the inner tube, for example, by laser welding the ends 360° about the circumference of the inner tube, to transmit torque from a motorized handpiece (not shown) to the bur tip 36 while allowing the flexible region 39 to conform to the angled, bent or curved shape of the outer member.

In a preferred embodiment, the inner tube is formed of Type 304L stainless steel tubing, ¾ hard, with an inner diameter of about 0.067 inch and an outer diameter of about 0.087 inch. Spiral cut 40 can be formed using any suitable technique but is preferably formed by laser cutting the tubing. In the preferred embodiment, the cut starts or begins about 0.59 inch proximally of the distal end of the bur tip and extends proximally about 0.89 inch to terminate or end about 1.48 inches proximally of the distal end of the bur tip. As a result, the inner tube can be bent immediately adjacent the adapter by which the bur tip is coupled to the inner tube as explained below. The cut is shown as a left hand spiral cut which, looking at FIG. 4, is oriented at an angle $\alpha$ of about 70° relative to the longitudinal axis of the inner tube. The width or kerf of the cut is preferably about 0.006 inch with a longitudinal spacing of about 0.062 inch between rings formed by the spiral cut.

In the preferred embodiment, the innermost strip is formed of Type 302 stainless steel flat strip, full hard, with a width of about 0.05 inch and a thickness of about 0.006 inch. Looking at FIG. 4, the innermost strip is wrapped at an angle $\beta$ of about 110° relative to the longitudinal axis of the inner tube. Opposite ends of the strip are secured to the inner tube, preferably by laser welding the ends completely, i.e. 360°, about the circumference of the tube. The spiral wrap formed by the innermost strip begins about 0.57 inch proximally of the distal end of the bur tip and extends proximally about 0.93 inch to terminate about 1.50 inches proximally of the distal end of the bur tip. As shown in FIGS. 2 and 4, the outermost strip is wrapped around the innermost strip in the same direction as the spiral cut. The outermost strip is preferably formed of the same material as the innermost strip and with the same configuration; however, the outermost strip is preferably oriented at the same angle $\alpha$ as the spiral cut. Opposite ends of the outermost strip are also preferably secured to the inner tube by laser welding the ends about the circumference of the tube. The spiral wrap formed by the outermost strip begins and ends the same distances proximally of the distal end of the bur tip as the spiral wrap formed by the innermost strip.

As best seen in FIGS. 2 and 4, the bur tip 36 is coupled to the inner tube via an adapter or coupling 46. However, it should be appreciated that the bur tip can be coupled or connected directly to the inner tube as disclosed in prior application Ser. No. 09/404,461 incorporated herein by reference. The bur tip 36 includes a bullet-shaped bur body 48 and a neck 49 extending proximally from the bur body 48 to be disposed within the adapter as explained further below. A plurality of flutes 50 are formed in the bur body to define cutting surfaces 52 emanating from the distal end 54 of the bur tip. The flutes 50 and, therefore, the cutting surfaces 52, extend longitudinally at an angle to a longitudinal axis of the bur tip. The flutes are formed so that the cutting surfaces 52 are curved or angled toward the clockwise direction looking proximally as shown in FIG. 5, and terminate at cutting edges 53. The neck 49 is of cylindrical configuration and is diametrically smaller than the bur body 48. The neck terminates at a proximal end defining a proximal end of the bur tip, and an annular groove 56 is formed in neck 49 between the proximal end thereof and bur body 48 as shown in FIG. 4. A passage 58 of uniform or constant diameter extends longitudinally, coaxially, entirely through the bur tip and has an opening or port 60 at the distal end 54 of the bur tip. The opening 60, which has a diameter the same as the diameter of passage 58, faces forwardly or to the front of the bur tip and defines a distal aspiration or suction port for the inner member.

It should be appreciated that any suitable bur tip configuration can be used including, but not limited to, configurations where the bur body is generally spherical, hemispherical, conical, pear shaped, round or cylindrical. Also, the cutting surfaces and edges can be formed in various ways and can have various configurations including fluted and diamond cut cutting surface and edge configurations. According to a preferred embodiment, six flutes having a 5 to 7 degree right hand helix, neutral to positive rake, are formed in the bur body. The bur tip has a length of about 0.34 inch with the body having a length of about 0.230 inch and the neck having a length of about 0.110 inch. The annular groove has a width of about 0.030 inch and begins about 0.280 inch proximally of the distal end of the bur tip. The passage through the bur tip has a diameter of about 0.037 inch. The bur tip is made of 440A stainless steel hardened to RC52/57.

The adapter 46, best shown in FIG. 6, comprises a hollow cylindrical or tubular member having a distal segment 62 of smaller external diameter joined, at a truncated conical junction, to a proximal segment 64 of larger external diameter. A passage or lumen 66 extends longitudinally, coaxially, entirely through the adapter, which therefore has open distal and proximal ends communicating with the passage 66. The passage 66 has a smaller diameter distal passage section 68 joined to a larger diameter proximal passage section 70 at an internal shoulder 72. The open distal end of the adapter is designed to receive the neck 49 of the bur tip while the open proximal end of the adapter is designed to receive the distal end 38 of the inner tube. An opening or port 74 is formed in the proximal segment 64 distally of the internal shoulder 72, the opening 74 facing laterally outwardly of the inner member and communicating with the passage 66. The opening 74 defines a proximal aspiration or suction port for the inner member.

In a preferred embodiment, the distal passage section has a diameter of about 0.078 inch to accept the neck of the bur tip, and the proximal passage section has a is; diameter of about 0.088 inch to accept the distal end of the inner tube. The adapter has a length of about 0.300 inch with the distal segment having a length of about 0.083 inch, the proximal segment having a length of about 0.200 inch and the junction having a length of about 0.017 inch. The distal segment has an outer diameter of about 0.102 inch, and the proximal segment has an outer diameter of about 0.1225 inch. The center of the opening or port 74 is about 0.374 inch from the distal end of the bur tip when the bur tip is assembled to the adapter. The adapter is made of 304 stainless steel with the proximal segment externally coated with Medcoat 2000, which is supplied by Electrolizing Corporation of Ohio.

The inner member is assembled by securing the neck of the bur tip to the distal end of the adapter and securing the distal end of the inner tube to the proximal end of the adapter. When so assembled, the passage through the bur tip, the passage through the adapter and the lumen of the inner tube are continuous with one another and define a continuous aspiration or suction passage entirely through the inner member. A preferred manner of assembling the inner member involves inserting the distal end of the inner tube into the proximal passage section of the adapter to abut the internal shoulder and laser welding the inner tube to the proximal end of the adapter. The preferred manner of assembly also involves inserting the neck of the bur tip in the distal passage section of the adapter so that the annular groove is disposed in the distal passage section with the bur body adjacent or spaced only slightly distally of the adapter distal end. Thereafter, the adapter is crimped and laser welded to the neck. In particular, the adapter is crimped at a location aligned with the annular groove of the neck so that the crimped portion 75 of the adapter enters and is disposed in the annular groove as shown in FIG. 4. Hub 32 is attached to inner tube 34 in a conventional manner using a raised fine diamond knurl at the proximal end of the inner tube as a point of attachment. In the preferred embodiment, the inner member has an overall length, prior to attachment to hub 32, of about 6.51 inches.

The outer hub 16 and inner hub 32 are designed for releasable or removable coupling with a powered surgical handpiece capable of rotating the inner member within the outer member while the outer member is rigidly secured to the handpiece. In the preferred embodiment, the hubs are designed for use with the STRAIGHTSHOT® handpiece of Xomed Surgical Products, Inc. of Jacksonville, Fla. and disclosed in U.S. Pat. No. 5,916,231 to Bays, the disclosure of which is incorporated herein by reference. The hubs 16 and 32 are therefore similar in major aspects to the hubs disclosed in the aforementioned U.S. Pat. No. 5,916,231.

The rotary bur instrument is assembled for use by inserting bur tip 36 of inner member 14 into the proximal end of outer hub 16 and advancing the inner member distally so that the bur tip is disposed externally of the distal end of the outer tube. When the inner member is fully inserted and advanced within the outer member, the proximal aspiration port 74 will be disposed proximally of the cutting edges or surfaces and will be disposed close to, adjacent or in alignment with the distal end of the outer member. In the preferred embodiment, the proximal aspiration port is substantially aligned with the peripheral edge of the outer tube to be exposed by the outer member a maximum amount when aligned with the center of recess 30 and to be exposed less than the maximum amount when not aligned with the recess as the inner member rotates within the outer member. More specifically, the proximal aspiration port is exposed by the outer tube the maximum amount when the inner member is in a rotational position wherein the proximal aspiration port is aligned with the recess and is exposed a minimum amount when the inner member is in a rotational position 180 degrees from the rotational position wherein the proximal aspiration port is aligned with the recess. The distal end of the irrigation passage is 180 degrees from the recess and, therefore, the proximal aspiration port is exposed the minimum amount when aligned with the distal end of the irrigation passage.

The maximum amount of exposure of the proximal aspiration port by the outer tube may correspond to total or partial exposure of the proximal aspiration port. The minimum amount of exposure of the proximal aspiration port by the outer tube may correspond to a partial exposure or no exposure of the proximal aspiration port. The overall length of the rotary bur instrument 10 as well as the presence of a bend in the outer tube, the location of the bend, the magnitude of the bend angle, the radius of curvature and other dimensions are dependent upon the type of surgery to be performed. For bone removal from a patient's nasal frontal beak, for example, the rotary bur instrument 10 preferably has an overall length of about 6.510 inches when assembled.

In use, hubs 16 and 32 are connected to a conventional motorized surgical handpiece (not shown), such as the STRAIGHTSHOT®) marketed by Xomed Surgical Products, Inc., such that the outer member 12 is held substantially stationary relative to the handpiece while permitting inner member 14 to rotate within the outer member. At this point, the inner member is disposed concentrically within the outer member, the adapter 46 acting as a bearing member or bearing surface within the outer tube to keep the inner member concentric while rotating. The flexible region 39 of the inner member is disposed within bend 22 of the outer member. When the handpiece motor is actuated, outer member 12 remains substantially stationary relative to the handpiece while inner member 14 is rotated. More specifically, actuation of the handpiece motor causes inner hub 32 to rotate. Inner tube 34 is rigidly attached to inner hub 32 and is thus rotated in the same direction as the hub with spiral cut 40 allowing the inner member to bend as it is rotated and spiral strips 42 and 44 reducing take-up when the direction of rotation is reversed. More specifically, if the hub is rotated in the same direction as the spiral cut, the innermost spiral strip of material wound over the inner tube will tend to unwind or expand radially and be resisted by radial contraction of the outermost spiral strip of material so that the torque can be transmitted immediately without any delay. If the hub is rotated in the direction opposite the spiral cut, the innermost spiral strip of material will tend to wind up and contract radially and be resisted by the inner tube so that torque can be transmitted immediately without any delay.

The instrument 10 is particularly adapted to allow surgical removal of bone from a patient's nasal frontal beak transseptally or ipsi-laterally. Irrigating fluid such as saline is supplied to the operative site or area via the open distal end of the irrigation tube as the inner member is rotated to effect resection of the bone. Also, suction applied through the inner member via the handpiece is applied at the operative site or area via the distal aspiration port at the distal end of the bur body and the proximal aspiration port disposed proximally of the bur body, since the passage through the bur tip, the passage through the adapter and the lumen of the inner tube form a continuous suction or aspiration passage. Since the proximal aspiration port is exposed the maximum amount when it is aligned with the recess in the peripheral edge of the outer member, maximum suction is applied at the operative site when the proximal aspiration port moves past the recess. Since the proximal aspiration port is exposed less than the maximum amount or is not exposed when it is aligned with the distal end of the irrigation tube, less suction or no suction is applied at the operative site when the proximal aspiration port is rotated past the distal end of the irrigation tube. In this manner, the discharge of irrigating fluid from the distal end of the irrigation tube is not significantly interrupted each time the proximal aspiration port is rotated past the distal end of the irrigation tube.

The bur tip produces both side and end cutting of the bone; however, most of the bone resection is obtained by side cutting with the longitudinal cutting edges rather than by end cutting with the distal end of the bur tip. The proximal aspiration port serves to aspirate or evacuate blood, saline and the majority of the resected bone, since most of the bone resection occurs along the flutes. The distal aspiration port serves to evacuate bone, blood and saline, but primarily blood and saline since less bone is resected at the distal end of the bur tip. The distal aspiration port thusly prevents the accumulation of fluids and bone fragments at the distal end of the bur tip and thereby enhances endoscopic visualization of the bur tip during the procedure. Suction provided by the distal aspiration port at the distal end of the bur tip is maintained while the inner member is rotated, providing enhanced visibility of the bur tip by an endoscope throughout the procedure. Clogging, although unexpected, can be cleared by removing the instrument from the operative site and pushing a stylette through the passage of the bur tip to reach the obstruction, which is easier, faster and less complicated to perform than the declogging procedures required for conventional rotary bur instruments.

An alternative rotary bur instrument according to the present invention is illustrated at 110 in FIG. 7. Rotary bur instrument 110 is similar to instrument 10 except that inner member 114 of instrument 110 is without a proximal aspiration port, the bearing member or surface for instrument 110 is provided with a flat, and the irrigation passage is defined between the inner member 114 and the outer member 112 of instrument 110 rather than by an external irrigation tube. Also, the flexible region 139 for inner member 114 is greater in length than flexible region 39, and the hubs 116 and 132 are designed somewhat differently than the hubs 16 and 32. The hub 116 for outer member 112 is provided with an optional nipple 176 extending proximally from a side of the hub at an acute angle relative to the longitudinal axis 126 of the proximal length portion 120. The nipple communicates with an annular space, gap or channel between the outer member 112 and the inner member 114 defining the irrigation passage when the inner member is disposed within the outer member. Accordingly, when a source of irrigating fluid is connected with the nipple, such as via a length of flexible tubing connected to the nipple, the fluid will be supplied to the bur tip 136 as made possible by a flat on the bearing member or surface. The fluid thusly supplied to the bur tip serves to prevent clogging of cut or abraded tissue aspirated through the lumen of inner member 114.

FIGS. 8 and 9 illustrate the adapter 146, i.e. the bearing member or surface, of the instrument 110 coupled to neck 149 of bur tip 136 and to inner tube 134 as described above for inner member 14. However, no aspiration port is provided in the adapter 146; and, accordingly, suction is applied at the operative site via aspiration passage 158 and the distal aspiration port 160 at the distal end of the bur tip. Also, as best shown in FIG. 10, the adapter 146 has a flat 178 thereon so that a gap or space is presented between the flat 178 and the outer tube 118 when the inner member is assembled with the outer member. The flat extends the entire length of the adapter proximal segment, and the gap formed thereby forms part of the irrigation passage allowing the irrigating fluid between the outer and inner members to flow past the adapter for discharge from the distal end of the outer member. The irrigating fluid is discharged towards the distal end of the bur tip; and, at the distal end of the bur tip, the distal aspiration port 160 aspirates the irrigating fluid, blood and bone through the suction passage of the inner member.

Use of a spiral wrap arrangement to impart flexibility to the inner members allows the inner tubes to be of relatively small diametric or cross-sectional size. Accordingly, the external diametric or cross-sectional size of the outer members can also be minimized. The preferred outer diameter for the outer members is about 0.146 inch, according to the preferred embodiments, which is approximately 1 mm less than the outer diameters of conventional angled rotary bur instruments. Minimization of the outer member external diameter as achieved with the present invention further improves surgeon visibility and increases the amount of free area available to the surgeon in which to maneuver the bur instruments and the endoscopes.

The rotary bur instruments of the present invention can be provided with or without bends, angles or curves. Where bends are provided, the location of the bends as well as the sizes of the bend angles can be varied depending on the procedure to be performed. For example, the bends of the instruments of the present invention may be located further distally than the bends of conventional angled rotary bur instruments for accessing anatomical areas that are inaccessible by conventional instruments. Since the inner tubes are flexible adjacent or close to the proximal ends of the adapters, the rotary bur instruments according to the present invention can be bent closer to the bur tips than prior art instruments to improve access to difficult to reach areas of the body in surgery of the head and neck and, in particular, nasal surgery. The present invention also reduces the number of parts needed to produce a flexible inner member for an angled rotary bur instrument by forming a helical or spiral cut in an inner tube and wrapping one or more strips of material around the spirally cut portion of the tube to improve the torque transmitting capabilities of the tube.

The rotary bur instruments according to the present invention can be bent anywhere along the length of the outer tubes so long as the inner tubes are provided with a flexible region located in juxtaposed relation to the bends. If desired, more complex curvatures and configurations can be formed by bending the outer tubes in more than one location and providing the inner tubes with one or more flexible regions in juxtaposed relation to the bends.

Where proximal aspiration ports are provided in the rotary bur instruments, suction provided at an operative site by the proximal aspiration ports can be controlled by controlling exposure of the proximal aspiration ports by the outer members. In particular, more or less of the proximal aspiration ports can be exposed or uncovered by the outer members to increase or decrease suction, respectively, at an operative site. Accordingly, the distal ends of the outer members can have various peripheral or circumferential edge configurations and/or the outer members can be of desired lengths to obtain a desired constant or variable amount of exposure of the proximal aspiration ports by the outer members as the inner members are rotated within the outer members.

The inner and outer hubs can be of conventional configuration to mate with any suitable handpiece and can be made of any relatively rigid, medically acceptable material. Proximal ends of the inner and outer members can be provided with knurled surfaces which extend about the circumference of the members to mate frictionally with the hubs.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A rotary bur instrument comprising
an elongate outer member including an outer tube having an open distal end; and
an elongate inner member rotatably disposed within said outer member and including an inner tube having a distal end, a lumen extending longitudinally therethrough and a bur tip disposed at said distal end of said inner tube extending distally from said open distal end of said outer tube, said bur tip having a distal end, a central longitudinal axis, a plurality of longitudinally extending flutes formed therein defining a plurality of cutting surfaces, a passage of uniform diameter extending longitudinally, entirely therethrough in communication with said lumen to define an aspiration passage through said inner member and a distal aspiration port at said distal end of said bur tip communicating with said aspiration passage, said distal aspiration port being coaxial with said central longitudinal axis and having a diameter the same as said uniform diameter.

2. A rotary bur instrument as recited in claim 1 wherein said lumen extends axially through said inner tube and said passage extends axially through said bur tip.

3. A rotary bur instrument as recited in claim 2 wherein said flutes emanate from said distal end of said bur tip.

4. A rotary bur instrument as recited in claim 3 wherein said flutes are disposed at an angle to said central longitudinal axis.

5. A rotary bur instrument as recited in claim 4 wherein said cutting surfaces are curved.

6. A rotary bur instrument as recited in claim 1 wherein said bur tip has a proximal end and said inner member further includes an adapter coupling said proximal end of said bur tip to said distal end of said inner tube.

7. A rotary bur instrument as recited in claim 6 wherein said bur tip includes a bur body and a neck extending proximally therefrom to a proximal end defining said proximal end of said bur tip and said adapter has an open distal end receiving said proximal end of said neck, an open proximal end receiving said distal end of said inner tube and a passage therethrough communicating with said passage of said bur tip and said lumen of said inner tube to define said aspiration passage.

8. A rotary bur instrument as recited in claim 7 wherein said adapter is crimped to said neck.

9. A rotary bur instrument as recited in claim 8 wherein said neck has an annular groove and said adapter is crimped at a location corresponding to said groove.

10. A rotary bur instrument as recited in claim 7 and further including a proximal aspiration port formed in said adapter and communicating with said aspiration passage.

11. A rotary bur instrument as recited in claim 8 wherein said adapter is welded to said neck and to said distal end of said inner tube.

12. A rotary bur instrument as recited in claim 1 wherein said inner member further includes a proximal aspiration port communicating with said aspiration passage and disposed proximally of said flutes.

13. A rotary bur instrument as recited in claim 12 wherein said proximal aspiration port faces laterally from said inner member and said distal aspiration port faces distally from said distal end of said bur tip.

14. A rotary bur instrument as recited in claim 1 and further including an irrigation passage disposed externally along said outer tube and having a distal end adjacent said distal end of said outer tube and a proximal end for being coupled with a source of irrigating fluid.

15. A rotary bur instrument as recited in claim 1 wherein an annular space is presented between said inner member and said outer member to define an irrigation passage for supplying irrigating fluid to said bur tip.

16. A rotary bur instrument as recited in claim 15 wherein said inner member further includes an adapter coupling said bur tip to said distal end of said inner tube and a flat on said adapter disposed within said outer tube by which the irrigating fluid can pass between said adapter and said outer member.

17. A rotary bur instrument as recited in claim 1 wherein said outer tube has proximal and distal portions connected by a bend, said inner tube includes a flexible region adjacent said bend, said flexible region is defined by a helical cut formed in said inner tube in a first direction and said inner member further includes a first strip of material spirally wound over said helical cut in a second direction opposite said first direction and a second strip of material spirally wound over said first strip of material in said first direction.

18. A rotary bur instrument as recited in claim 17 wherein opposite ends of said first strip are secured to said inner tube on opposite sides of said helical cut and opposite ends of said second strip are secured to said inner tube on opposite sides of said first strip.

19. A rotary bur instrument as recited in claim 18 wherein said helical cut and said second strip are each oriented at a first angle relative to a longitudinal axis of said inner tube and said first strip of material is oriented at a second angle which is the supplement of said first angle.

20. A rotary bur instrument as recited in claim 19 wherein said bend has an angle of about 40 degrees.

21. A rotary bur instrument as recited in claim 19 wherein said outer tube has an external diametric size of about 0.146 inch.

22. A rotary bur instrument comprising
an outer member including an outer tube having an open distal end; and
an inner member rotatably disposed within said outer member and including a longitudinal aspiration passage therethrough, an inner tube having a distal end, a bur tip disposed at said distal end of said inner tube and including a bur body disposed distally of said open distal end of said outer tube, said bur tip having a distal end at which said bur body terminates, a proximal end, a plurality of cutting edges separated by flutes formed in said bur body, and a passage extending longitudinally, entirely therethrough forming part of said aspiration passage, a distal aspiration port at said distal end of said bur tip communicating with said aspiration passage, and a proximal aspiration port disposed proximally of said bur body communicating with said aspiration passage, said passage having a uniform diametric size, said distal aspiration port facing distally from said distal end of said bur tip and having a diametric size the same as said diametric size of said passage.

23. A rotary bur instrument as recited in claim 22 wherein said aspiration passage extends axially through said inner member.

24. A rotary bur instrument as recited in claim 23 wherein said inner member includes a hub secured to a proximal end of said inner tube and said aspiration passage extends entirely through said hub.

25. A rotary bur instrument as recited in claim 22 wherein said proximal aspiration port is disposed adjacent said distal end of said outer tube.

26. A rotary bur instrument as recited in claim 25 wherein said proximal aspiration port is disposed proximally of said cutting edges.

27. A rotary bur instrument as recited in claim 26 wherein said inner member further includes an adapter coupling said bur tip to said distal end of said inner tube and having a passage entirely therethrough forming part of said aspiration passage, and said proximal aspiration port is formed in said adapter.

28. A rotary bur instrument as recited in claim 25 wherein said distal end of said outer tube is defined by a peripheral edge and said peripheral edge has a recess therein through which said proximal aspiration port is exposed when said inner member is in a rotational position wherein said proximal aspiration port is aligned with said recess.

29. A rotary bur instrument as recited in claim 28 wherein said proximal aspiration port is exposed by said outer tube a maximum amount when said inner member is in said rotational position wherein said proximal aspiration port is aligned with said recess and less than said maximum amount when said inner member is in a rotational position wherein said proximal aspiration port is not aligned with said recess.

30. A rotary bur instrument as recited in claim 29 wherein said proximal aspiration port is exposed by said outer tube a minimum amount when said inner member is in said rotational position wherein said proximal aspiration port is not aligned with said recess and said rotational position wherein said proximal aspiration port is not aligned with said recess is 180 degrees from said rotational position wherein said proximal aspiration port is aligned with said recess.

31. A rotary bur instrument as recited in claim 29 and further including an irrigation passage extending along said outer member and having a distal end from which irrigating fluid is discharged, said proximal aspiration port being aligned with said distal end of said irrigation passage when said inner member is in said rotational position wherein said proximal aspiration port is not aligned with said recess.

32. A rotary bur instrument as recited in claim 31 wherein said proximal aspiration port is exposed by said outer tube a minimum amount when said inner member is in said rotational position wherein said proximal aspiration port is not aligned with said recess.

33. A rotary bur instrument as recited in claim 31 wherein said rotational position wherein said proximal aspiration port is not aligned with said recess is 180 degrees from said rotational position wherein said proximal aspiration port is aligned with said recess.

34. A rotary bur instrument comprising
an outer member including a rigid outer tube having proximal and distal portions connected by a bend and having an open distal end; and
an inner member rotatably disposed within said outer member and including an inner tube having a distal end, a lumen extending longitudinally therethrough and a flexible region adjacent said bend, and a bur tip disposed at said distal end of said inner tube extending distally from said open distal end of said outer tube, said bur tip terminating at a distal end defined by a distal end wall, said bur tip having a passage of constant diameter extending longitudinally, entirely therethrough in communication with said lumen to define an aspiration passage through said inner member and a distal aspiration port at said distal end of said bur tip communicating with said aspiration passage, said distal aspiration port being formed through said distal end wall and having a diameter the same as said diameter of said passage.

35. A rotary bur instrument as recited in claim 34 wherein said flexible region is defined by a helical cut formed in said inner tube in a first direction and said inner member further includes a first strip of material spirally wound over said helical cut in a second direction opposite said first direction and a second strip of material spirally wound over said first strip of material in said first direction.

36. A rotary bur instrument as recited in claim 34 wherein said bur tip includes a bur body and a neck extending proximally therefrom to a proximal end of said bur tip and said inner member further includes an adapter coupling said proximal end of said bur tip to said distal end of said inner tube, said adapter having an open distal end receiving said proximal end of said bur tip, an open proximal end receiving said distal end of said inner tube and a passage therethrough communicating with said passage of said bur tip and said lumen of said inner tube to define said aspiration passage.

37. A rotary bur instrument as recited in claim 36 and further including a proximal aspiration port formed in said adapter and communicating with said aspiration passage.

38. A rotary bur instrument as recited in claim 34 wherein said bur tip includes a plurality of flutes defining cutting surfaces emanating from said distal end of said bur tip.

39. A rotary bur instrument as recited in claim 38 wherein said inner member further includes a proximal aspiration port communicating with said aspiration passage and disposed proximally of said cutting surfaces.

40. A rotary bur instrument as recited in claim 39 wherein said distal end of said outer tube is defined by a peripheral edge and said peripheral edge has a recess therein through which said proximal aspiration port is exposed when said inner member is in a rotational position wherein said proximal aspiration port is aligned with said recess.

41. A rotary bur instrument as recited in claim 40 wherein said proximal aspiration port is exposed by said outer tube a maximum amount when said inner member is in said rotational position wherein said proximal aspiration port is aligned with said recess and less than said maximum amount when said inner member is in a rotational position wherein said proximal aspiration port is not aligned with said recess.

42. A rotary bur instrument as recited in claim 41 and further including an irrigation passage extending along said outer member and having a distal end from which irrigating fluid is discharged, said proximal aspiration port being aligned with said distal end of said irrigation passage when said inner member is in said rotational position wherein said proximal aspiration port is not aligned with said recess.

43. A rotary bur instrument as recited in claim 42 wherein said rotational position wherein said proximal aspiration port is not aligned with said recess is 180 degrees from said rotational position wherein said proximal aspiration port is aligned with said recess.

44. A rotary bur instrument as recited in claim 34 and further including an irrigation passage disposed externally along said outer tube and having a distal end adjacent said distal end of said outer tube and a proximal end for being coupled with a source of irrigating fluid.

45. A rotary bur instrument as recited in claim 34 wherein an annular space is presented between said inner member and said outer member to define an irrigation passage for supplying irrigating fluid to said bur tip.

46. A rotary bur instrument as recited in claim 45 wherein said inner member further includes an adapter coupling said bur tip to said distal end of said inner tube and a flat on said adapter disposed within said outer tube by which the irrigating fluid can pass between said adapter and said outer member.

47. A rotary bur instrument as recited in claim 34 wherein said bend has an angle of about 40 degrees.

48. A rotary bur instrument as recited in claim 34 wherein said outer tube has an external diametric size of about 0.146 inch.

* * * * *